US012569013B2

(12) United States Patent
Johal

(10) Patent No.: US 12,569,013 B2
(45) Date of Patent: Mar. 10, 2026

(54) GARMENT WITH DIAPER SUPPORT

(71) Applicant: Sonia Johal, Richmond (CA)

(72) Inventor: Sonia Johal, Richmond (CA)

(73) Assignee: Sonia Johal, Richmond (CA)

( * ) Notice: Subject to any disclaimer, the term of this patent is extended or adjusted under 35 U.S.C. 154(b) by 0 days.

(21) Appl. No.: 18/537,791

(22) Filed: Dec. 12, 2023

(65) Prior Publication Data

US 2024/0196995 A1 Jun. 20, 2024

Related U.S. Application Data

(60) Provisional application No. 63/387,482, filed on Dec. 14, 2022.

(51) Int. Cl.
*A41B 13/00* (2006.01)
*A61F 13/56* (2006.01)

(52) U.S. Cl.
CPC ........ *A41B 13/005* (2013.01); *A61F 13/5622* (2013.01)

(58) Field of Classification Search
CPC ....... A41B 13/04; A41B 13/06; A41B 13/005; A61F 13/5622
USPC .............................................................. 2/80
See application file for complete search history.

(56) References Cited

U.S. PATENT DOCUMENTS

| | | | | | |
|---|---|---|---|---|---|
| 348,181 | A | * | 8/1886 | Agnew | A61F 13/64 604/394 |
| 648,940 | A | * | 5/1900 | Guinzburg | A41B 13/08 2/111 |
| 770,394 | A | * | 9/1904 | Seitz | A41B 13/08 2/111 |
| 788,259 | A | * | 4/1905 | Guinzburg | A41B 13/08 2/112 |
| 881,640 | A | * | 3/1908 | Wimmel | A61F 13/64 604/394 |
| 1,311,600 | A | * | 7/1919 | Fiore | A41B 13/00 D2/776 |
| 1,329,119 | A | * | 1/1920 | George | A41B 13/04 604/394 |
| 1,403,030 | A | * | 1/1922 | Janzow | A41D 11/00 2/75 |
| 1,411,816 | A | * | 4/1922 | Thomas | A41D 11/00 2/80 |

(Continued)

FOREIGN PATENT DOCUMENTS

| | | | | | |
|---|---|---|---|---|---|
| JP | 3132215 | U | * | 6/2007 | |
| KR | 20000030815 | A | * | 6/2000 | |
| KR | 101226836 | B1 | * | 1/2013 | ........... A61F 13/505 |

*Primary Examiner* — Heather Mangine
*Assistant Examiner* — Raquel M. Weis

(57) ABSTRACT

Examples of a baby garment with diaper support are described. The diaper support comprises a back panel and a front panel. The back panel is connected to the inner side of a back part of a garment along a waist portion. The front panel is connectable to an inner side of the front part of the garment along the front part of the waist portion. The diaper support further has a fastener with a first element and a corresponding second element. When the first and the second elements are separated, the diaper support is in an open configured to allow a user to put on a diaper and when the first and the second elements are joined together, the diaper support in in a close configuration supporting a weight of the diaper.

9 Claims, 5 Drawing Sheets

(56)                 References Cited

U.S. PATENT DOCUMENTS

| | | | | | |
|---|---|---|---|---|---|
| 1,413,459 | A | * | 4/1922 | Cunningham | A41B 13/08 |
| | | | | | 2/111 |
| 1,473,500 | A | * | 11/1923 | Mowrer | A41B 9/04 |
| | | | | | 2/400 |
| 1,758,081 | A | * | 5/1930 | Masters | A41B 13/00 |
| | | | | | 2/75 |
| 1,931,357 | A | * | 10/1933 | Potwin | A61F 13/78 |
| | | | | | 604/401 |
| 2,028,602 | A | * | 1/1936 | Hanson | A41B 13/08 |
| | | | | | 2/70 |
| 2,034,312 | A | * | 3/1936 | Rubin | A41D 1/06 |
| | | | | | 2/404 |
| 2,374,299 | A | * | 4/1945 | O'Hara | A41B 13/06 |
| | | | | | 5/413 R |
| 2,418,050 | A | * | 3/1947 | Shank | A41B 13/08 |
| | | | | | D2/743 |
| 2,469,556 | A | * | 5/1949 | Jacobson | A41B 13/005 |
| | | | | | 2/69.5 |
| 2,520,357 | A | * | 8/1950 | Brennan | A41B 13/06 |
| | | | | | D2/733 |
| 2,521,020 | A | * | 9/1950 | Prescott | A41D 11/00 |
| | | | | | 2/70 |
| 2,522,421 | A | * | 9/1950 | Wolf | A41B 9/08 |
| | | | | | 2/71 |
| 2,523,416 | A | * | 9/1950 | Brennan | A41B 13/005 |
| | | | | | D2/745 |
| 2,575,163 | A | * | 11/1951 | Donovan | A41B 13/04 |
| | | | | | 604/397 |
| 2,599,769 | A | * | 6/1952 | Macrae | A41D 1/089 |
| | | | | | 2/404 |
| 2,621,336 | A | * | 12/1952 | Wendroff | A41B 13/005 |
| | | | | | 2/227 |
| 2,651,781 | A | * | 9/1953 | Buchholz | A41B 13/06 |
| | | | | | 2/69.5 |
| 2,663,873 | A | * | 12/1953 | Stern | A41B 13/005 |
| | | | | | D2/744 |
| 2,691,983 | A | * | 10/1954 | Bernard | A61F 13/68 |
| | | | | | 604/397 |
| 2,695,615 | A | * | 11/1954 | Victor | A41B 13/04 |
| | | | | | 604/394 |
| 2,733,715 | A | * | 2/1956 | Folk | A41B 13/04 |
| | | | | | 604/401 |
| 2,825,906 | A | * | 3/1958 | Stumpf | A41B 13/04 |
| | | | | | 2/212 |
| 2,837,095 | A | * | 6/1958 | Stevenson | A41B 13/04 |
| | | | | | 604/385.13 |
| 2,839,058 | A | * | 6/1958 | Biever | A41B 13/04 |
| | | | | | 604/395 |
| 2,876,455 | A | * | 3/1959 | Harmon | A41B 13/00 |
| | | | | | 2/80 |
| 3,180,336 | A | * | 4/1965 | Bett | A41D 10/00 |
| | | | | | 2/400 |
| 3,641,997 | A | * | 2/1972 | Posey, Jr. | A61F 5/3784 |
| | | | | | 128/874 |
| 5,033,121 | A | * | 7/1991 | Larsen | A41B 9/008 |
| | | | | | 2/115 |
| 6,108,823 | A | * | 8/2000 | Danes | A41B 13/04 |
| | | | | | 2/403 |
| 6,223,352 | B1 | * | 5/2001 | Watlington | A41D 15/002 |
| | | | | | 2/83 |
| 6,243,871 | B1 | * | 6/2001 | Fidler | A41D 15/002 |
| | | | | | 2/111 |
| 6,266,822 | B1 | * | 7/2001 | Joyce | A47G 9/083 |
| | | | | | 2/69.5 |
| 6,668,382 | B1 | * | 12/2003 | Wright | C08F 236/20 |
| | | | | | 2/69.5 |
| 7,124,448 | B2 | * | 10/2006 | Davenport | A41F 9/02 |
| | | | | | 2/229 |
| 7,344,526 | B2 | * | 3/2008 | Yang | A61F 13/505 |
| | | | | | 2/919 |
| 7,491,196 | B2 | * | 2/2009 | Franke | A61F 13/496 |
| | | | | | 604/397 |
| 7,908,671 | B2 | * | 3/2011 | Gaugler | A41D 15/002 |
| | | | | | 2/69.5 |
| 7,993,322 | B2 | * | 8/2011 | Brud | A61F 13/66 |
| | | | | | 604/397 |
| 8,966,667 | B2 | * | 3/2015 | Peck | A41D 31/185 |
| | | | | | 2/227 |
| 9,179,712 | B2 | * | 11/2015 | Jaggernauth | A41B 13/08 |
| 9,204,673 | B1 | * | 12/2015 | Alperin | A41B 13/005 |
| 9,204,676 | B2 | * | 12/2015 | Gbadamosi | A41D 27/201 |
| 10,945,468 | B1 | * | 3/2021 | Hamilton | A41D 1/06 |
| 11,419,366 | B2 | * | 8/2022 | Kassel | A41B 13/08 |
| 11,439,545 | B2 | * | 9/2022 | Ramos | A61F 13/505 |
| 2008/0065039 | A1 | * | 3/2008 | Labit | A61F 13/5633 |
| | | | | | 604/385.15 |
| 2010/0043115 | A1 | * | 2/2010 | Weatherill | A41B 1/04 |
| | | | | | 2/243.1 |
| 2010/0168709 | A1 | * | 7/2010 | Hodgkin | A61F 13/5638 |
| | | | | | 604/386 |
| 2010/0299802 | A1 | * | 12/2010 | Bailey | A41F 19/005 |
| | | | | | 2/269 |
| 2011/0179556 | A1 | * | 7/2011 | Partovi | A41D 1/08 |
| | | | | | 2/243.1 |
| 2015/0101100 | A1 | * | 4/2015 | Flowers | A41B 13/06 |
| | | | | | 2/69.5 |
| 2016/0050979 | A1 | * | 2/2016 | Cartozian | A41B 13/005 |
| | | | | | 2/70 |
| 2016/0050980 | A1 | * | 2/2016 | Cartozian | A41B 1/06 |
| | | | | | 2/70 |
| 2016/0279001 | A1 | * | 9/2016 | Price | A61F 13/5622 |
| 2018/0027896 | A1 | * | 2/2018 | Stobar | A41B 13/005 |
| 2018/0070662 | A1 | * | 3/2018 | Yancie | A41B 9/12 |
| 2019/0254357 | A1 | * | 8/2019 | Yabsley | A41B 13/08 |
| 2019/0343191 | A1 | * | 11/2019 | Kassel | A41B 13/00 |
| 2020/0154790 | A1 | * | 5/2020 | Cleary | A41B 9/001 |
| 2024/0196995 | A1 | * | 6/2024 | Johal | A41B 13/005 |

* cited by examiner

GARMENT WITH DIAPER SUPPORT

CROSS REFERENCE TO RELATED APPLICATIONS

This application claims priority of U.S. Provisional Patent Application No. 63/387,482 filed Dec. 14, 2022, which is incorporated herein by reference.

TECHNICAL FIELD

The present disclosure generally relates to a baby garment and more particularly to a diaper support and a baby garment with a diaper support.

BACKGROUND

Unless otherwise indicated herein, the materials described in this section are not prior art to the claims in this application and are not admitted to be prior art by inclusion in this section.

Baby garments, like loose fitting jump suits or onesie, do not have a diaper support or underwear that supports the diaper when the baby wears it, so the diaper can slip down or can be uncomfortable for the baby. In order to provide the support for the diaper, the baby needs to wear an additional piece of clothing, for example, an underwear or short onesie, under the jump suit, which may be uncomfortable for the baby or leave the baby feeling overstuffed and overheated.

SUMMARY

In one aspect, a baby garment is provided. The baby garment comprises a body having a front part and a back-part joined together forming a torso portion of the garment with a head opening and two arm openings, a lower portion covering the lower extremities of the baby with a closable opening along a bottom edge of the lower portion and a waist portion between the torso portion and the lower portion of the garment. The body of the garment has an outer side and an inner side. The baby garment also comprises a diaper support that has a back panel with an outer face and an inner face that comprises a top edge, two side edges and a lower part. The back panel is connected to the inner side of the back part of the body at the waist portion along at least the top edge. The diaper support of the baby garment further comprises a front panel that is connectable to an inner side of the front part of the body at the waist portion and/or side parts of the front part. A two-part fastener is also provided with a first element and a corresponding second element. When the first and the second elements are separated, the diaper support is in an open configuration to allow a user to put on a diaper to be worn by a wearer. When the first and the second elements are joined together, the diaper support in in a closed configuration and can now support the weight of the diaper.

In one aspect, the lower part of the back panel and the lower part of the front panel are interconnected, forming an integral single panel. The first element of the fastener is positioned on the outer face of the front panel in proximity to the top edge and the second element of the fastener is positioned at the inner side of the front part of the garment along a part of the waist portion.

In another aspect, the first element of the fastener is positioned on the outer face in proximity to the lower part of the back panel of the diaper support and the second element of the fastener is positioned on the inner face in proximity to the lower part of the front panel. The front panel is connected to the inner side of the front part of the body at the waist portion along at least the top edge.

In one aspect a diaper support is provided. The diaper support comprises a back panel that has an outer face and an inner face and comprises a top edge, two side edges and a lower part. The back panel is connected to the inner side of a back part of a garment along a waist portion. The diaper support of the baby garment further comprises a front panel that is connected to an inner side of the front part of the garment along the front part of the waist portion and a fastener with a first element and a corresponding second element. When the first and the second elements are separated, the diaper support is in an open configuration to allow a user to put on a diaper, and when the first and the second elements are joined together, the diaper support is in a closed configuration supporting a weight of the diaper.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

DETAILED DESCRIPTION OF SPECIFIC EMBODIMENTS

The present invention discloses a piece of apparel or garment that incorporates integrated diaper support therein to support the weight of the diaper so it is more comfortable for the wearer. The garment can be a baby or toddler garment but is not limited to the baby garments. For example, the garment can be a jump suit, onesie, trousers, sleeping garment, dress, skirt or any similar piece of apparel.

Figure 1:
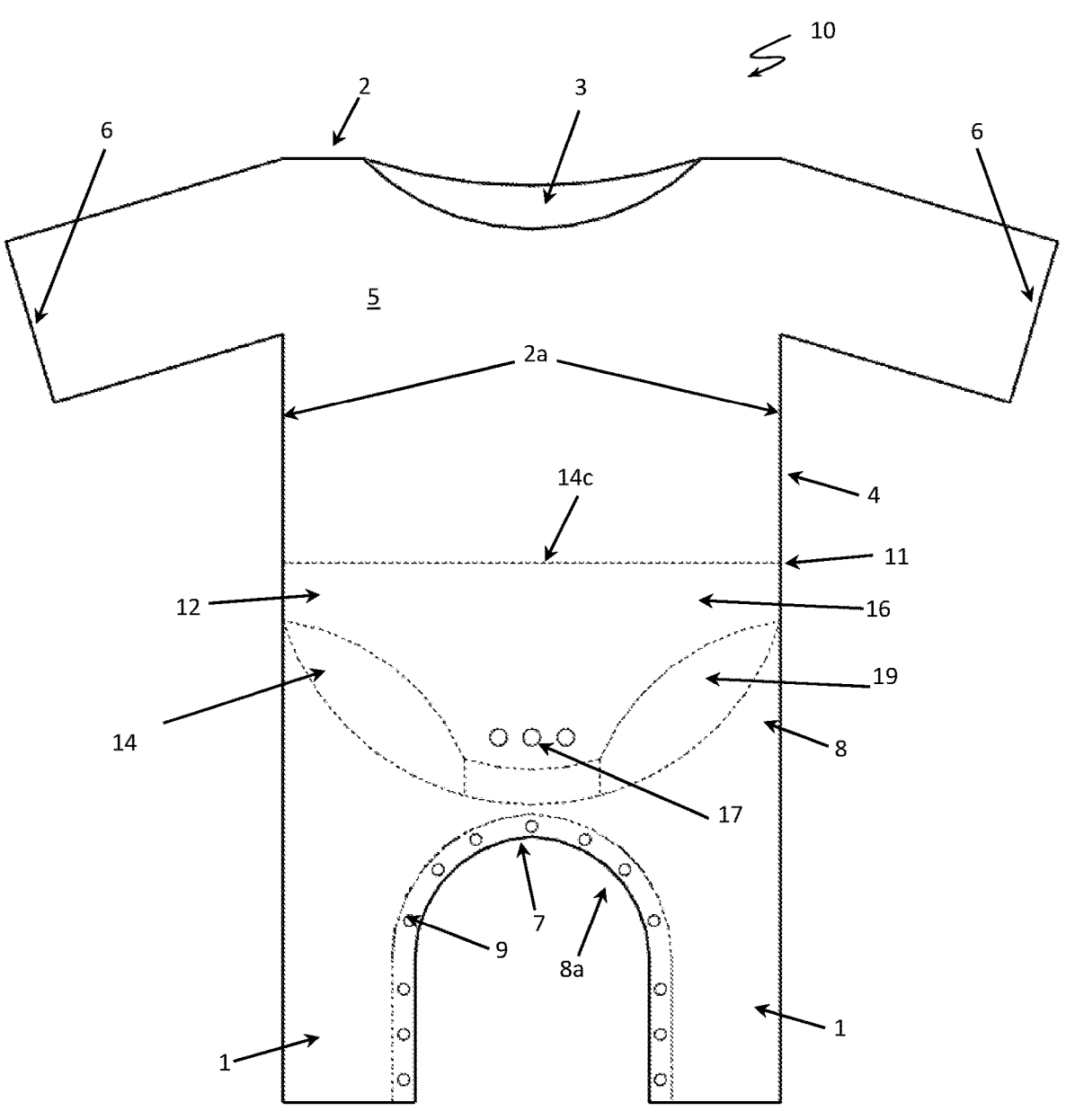
FIG. 1 is a front view of an example of a garment with one example embodiment of a diaper support.

FIG. 1 illustrates an example of a baby garment 10 with a diaper support 12. In the illustrated example the garment 10 is a baby jump suit or onesie but it can be any other suitable piece of apparel. The garment 10 can comprise a body 2 with a front part 4 and a back part (not shown) that are joined together to form the body 2 with a head opening 3, two arm openings 6 and two leg openings. The front and the back part of the garment 10 are joined together at least at side seams 2a (in some implementations) to form a torso portion 5 of the garment with the head opening 3 and the two arm openings 6, a lower portion 8 that covers the lower extremities of the wearer and a waist portion 11 between the torso portion 5 and the lower portion 8 of the garment 10. The lower portion 8 of the garment 10 can have a closable opening 7 along a bottom edge 8a of the lower portion 8 of the body 2. For example, a fastener 9 can be provided at the bottom edge to open and close the lower portion 8 of the garment 10. The lower portion 8 can be shaped so that when the fastener 9 is closing the lower portion 8, it forms the two legs openings and two legs portions 1 of the garment 10. The fastener 9 can be a zipper, a number of snap fasteners, a number of buttons with corresponding button openers or any other suitable fastener. The body 2 of the garment 10 has an inner side facing the skin of the wearer and an outer side facing the outside.

The diaper support 12 is provided on the inner side of the body 2 of the garment 10. The diaper support 12 can have a back panel 14 and a front panel 16. The back and the front panels 14, 16 both have an outer face 14a, 16a and an inner face 14b, 16b (see FIG. 3). The panels 14, 16 also have a top edge 14c, 16c, two side edges 14d, 16d and a lower part 14e, 16e. The back panel is connected to the inner side of the back part of the body 2 in proximity to the waist portion 11 along at least the top edge 14c. For example, the back panel 14 can be sewn or bonded to the inner side of the back part of the body 2 along the top edge 14c. In one embodiment, the back panel 14 can also be connected to the body 2 along at least a portion of the two side edges 14d. For example, an upper portion of the two side edges 14d can be sewn along a facing portion of the side seams 2a of the body 2.

The front panel 16 is also connectable to the inner side of the front part 4 of the body 2 in proximity to the waist portion 11. In the embodiment illustrated in FIG. 1, the front panel 16 is sewn or bonded to the inner side of the front part 4 of the body 2 along the top edge 16c. In one embodiment, the front panel 16 can also be connected to the body 2 along at least a portion of the two side edges 16d. For example, an upper portion of the two side edges 16d can be sewn along a facing portion of the side seams 2a of the body 2. In some implementations, the back panel 14 can be connected to the inner side of the back part of the body 2 only along the top edge 14c and the front panel 16 can be connected to the inner side of the front part 4 only along the top edge 16c. In one embodiment, the back panel 14 and the front panel 16 can be connected together along an upper portion of the respective side edges 14d, 16d.

The back panel 14 and the front panel 16 can be two separate panels that can be connectable using a diaper support fastener 17. The fastener 17 can be a two-part fastener having a first element 17a and a second element 17b. The first element 17a can be connected to the lower part 14e of the back panel 14 while the second element 17b of the diaper fastener 17 can be connected to the lower part 16e of the front panel 16. When the first and the second elements 17a, 17b are separated the diaper support 12 is in an open configuration to allow a user to put or change a diaper. When the first and the second elements 17a, 17b are joined together the diaper support 12 is in a closed configuration forming two legs openings 19 and supporting the weight of the diaper. For example, the first element 17a of the fastener can be on the outer face 14a in proximity to the lower part 14e of the back panel 14 of the diaper support 12, and the second element 17b of the fastener 17 is on the inner face 16b in proximity to the lower part 16e of the front panel 16 or vice-versa. For example, the fastener 17 is a snap fastener and the first element 17a can comprise a number of male parts of the snap fastener while the second element 17b comprises a number of matching female parts of the snap fastener. In another example, the first element 17a can comprise a number of buttons and the second element 17b can comprise a number of corresponding openings/slits. Persons skilled in the art would understand that any other suitable fastener 17 (e.g., hook and eye, etc.) can be used without departing from the scope of invention. For example, the two-part fastener 17 can be a snap fastener, a swan hook fastener, a Velcro® type of fastener, hook and loop fastener, hook and eye fastener, button and loop fastener, clasp and hook, or a buckle. In one embodiment, the two-part fastener 17 can be adjustable by having two or more numbers and/or rows of the first elements 17a and/or two or more numbers and/or rows of second elements 17b, so that a size of the diaper support 12 can be adjusted.

Figure 2:
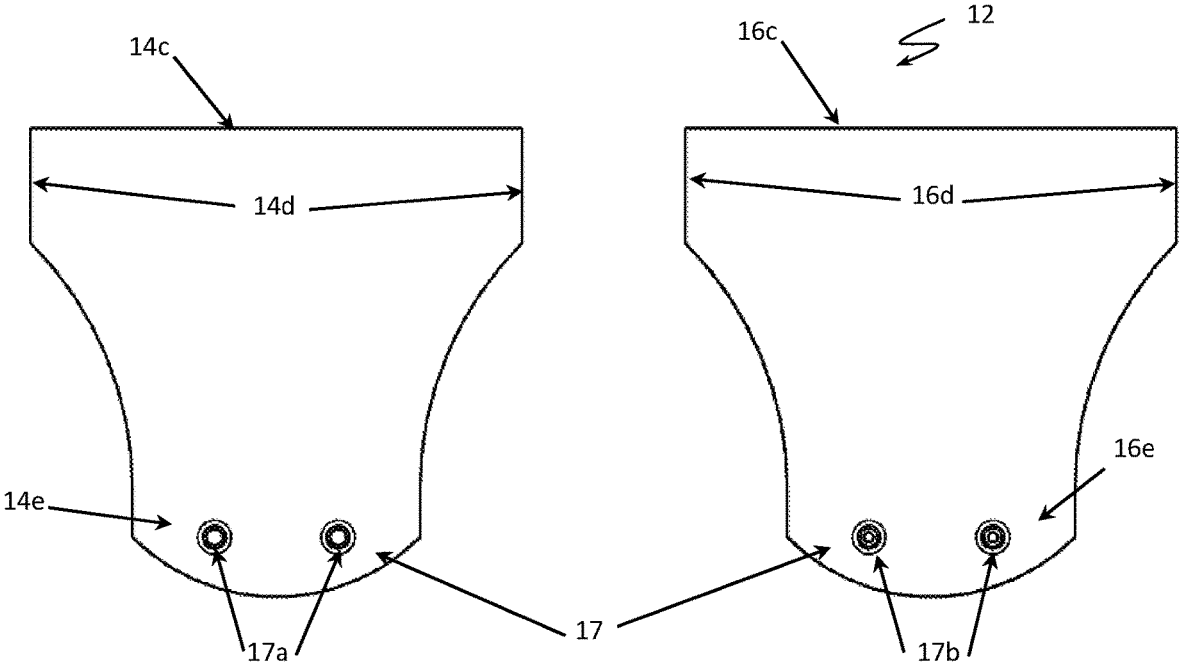
FIG. 2 is a top view of a first panel and a second panel of the diaper support of FIG. 1.
Figure 3:
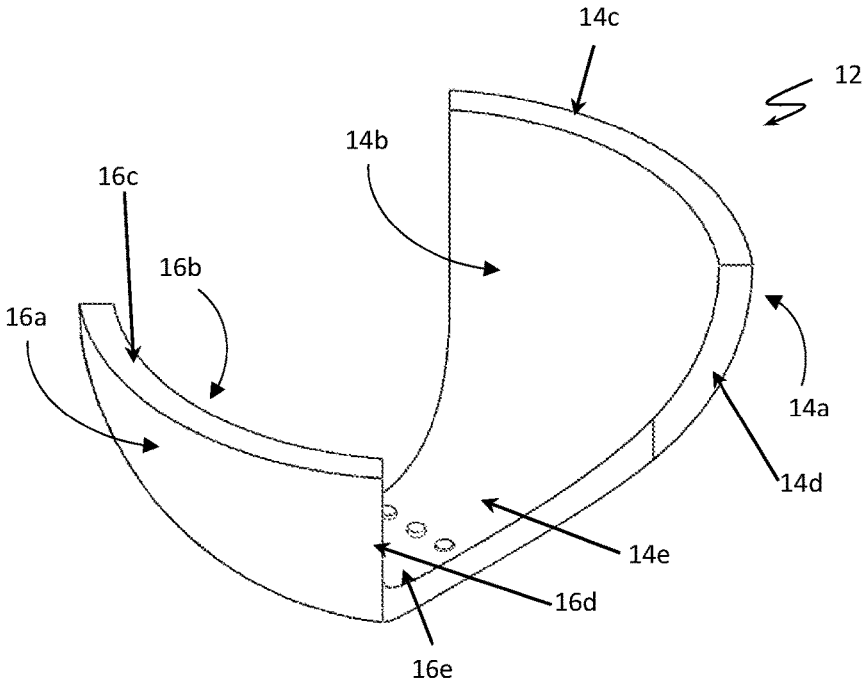
FIG. 3 is a perspective view of the diaper support of FIG. 1.

FIG. 2 and FIG. 3 show in more details the diaper support 12 and its back and front panels 14, 16 when not connected to the garment 10. FIG. 3 shows the diaper support 12 in closed configuration.

Figure 4:
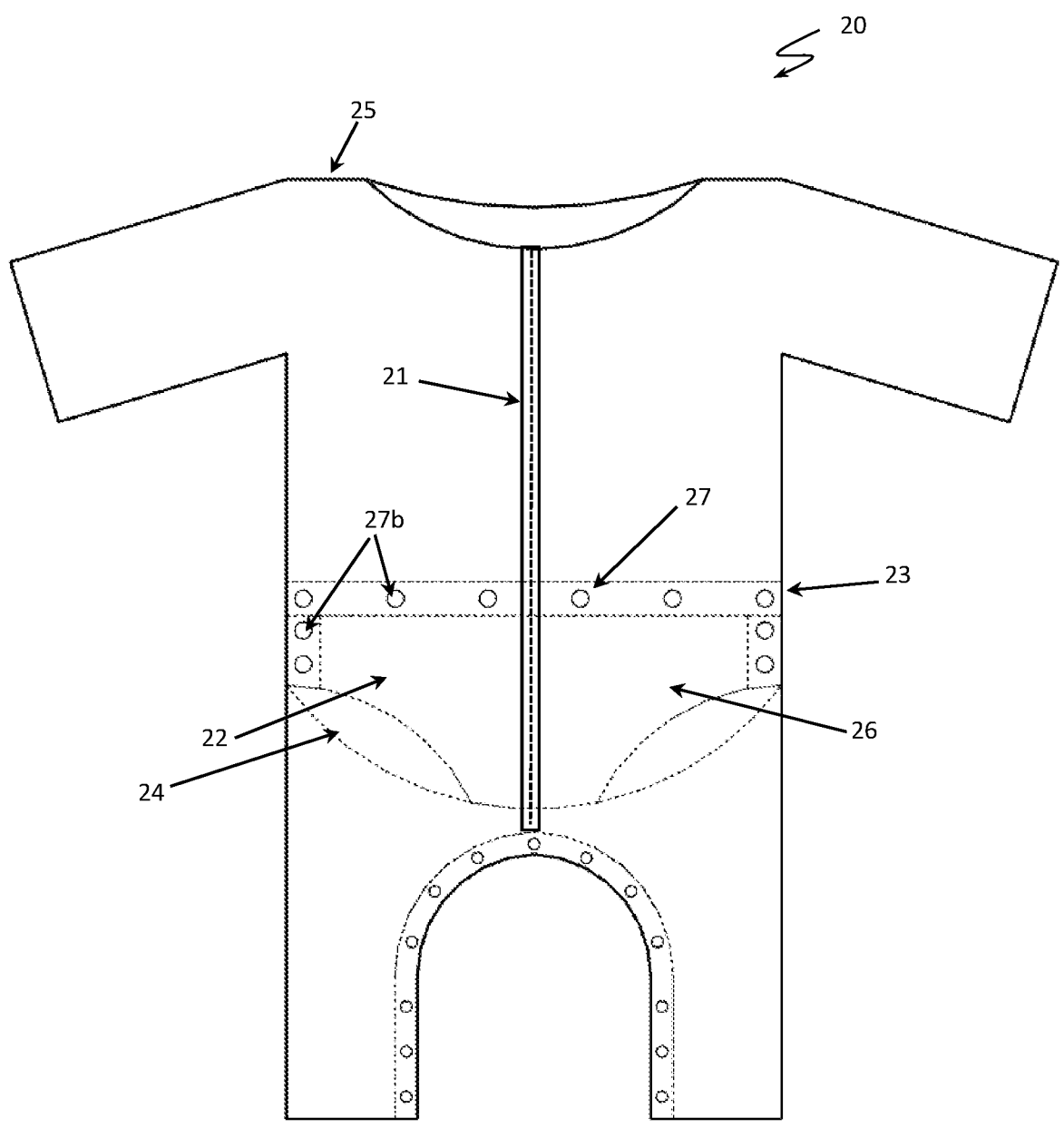
FIG. 4 is a front view of an example of a garment with another example embodiment of a diaper support.
Figure 5:
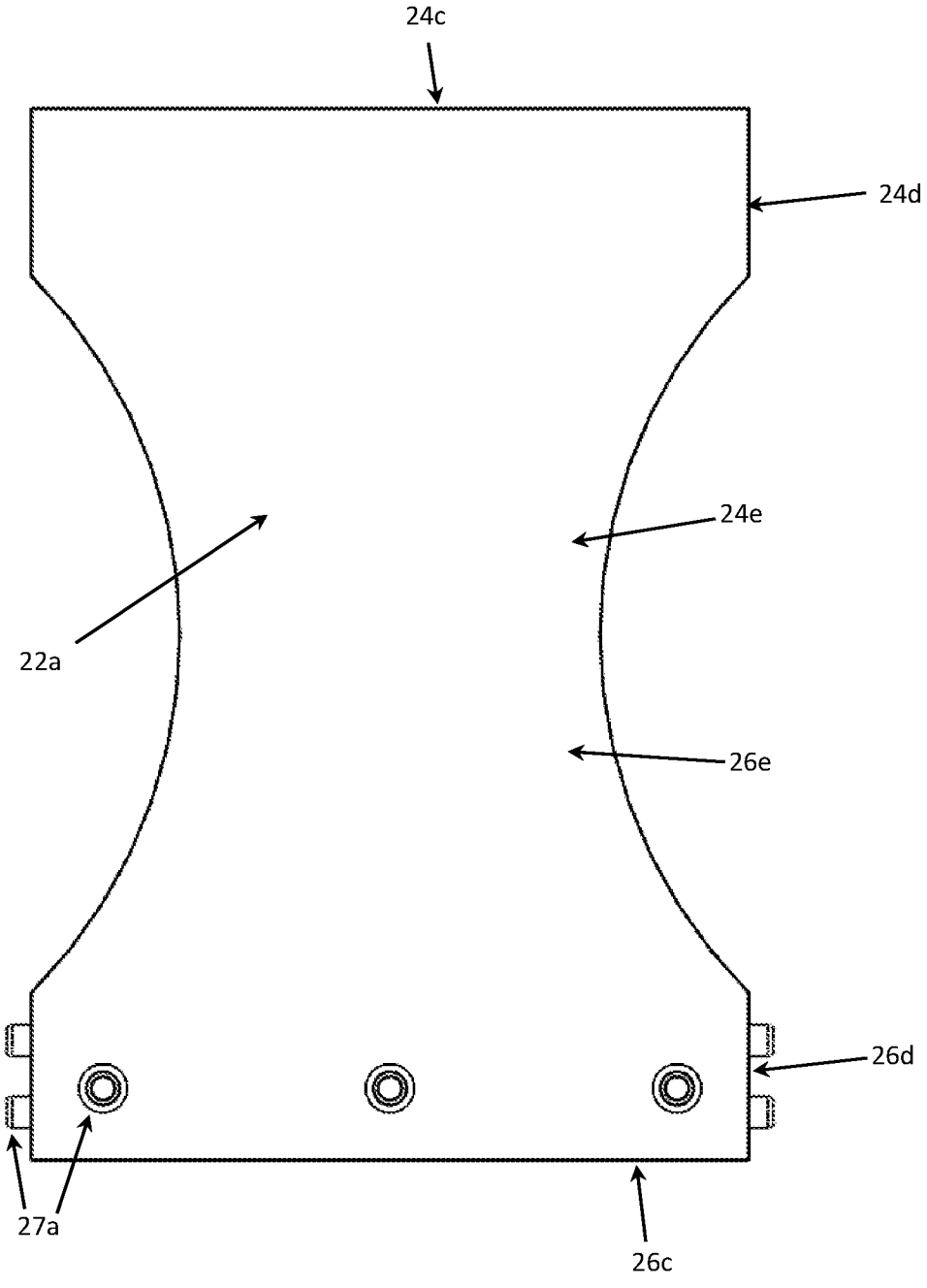
FIG. 5 is a top view the single panel diaper support of FIG. 4.

FIG. 4 illustrates another example of a baby garment 20 with a diaper support 22. The garment 20 can be similar to the garment 10 of FIG. 1 with the addition of a front closable opening 21. The front opening 21 can be opened and closed using any suitable fastener, such as zipper or a number of buttons arranged along the longitudinal axis of the opening 21, etc.

Figure 6:
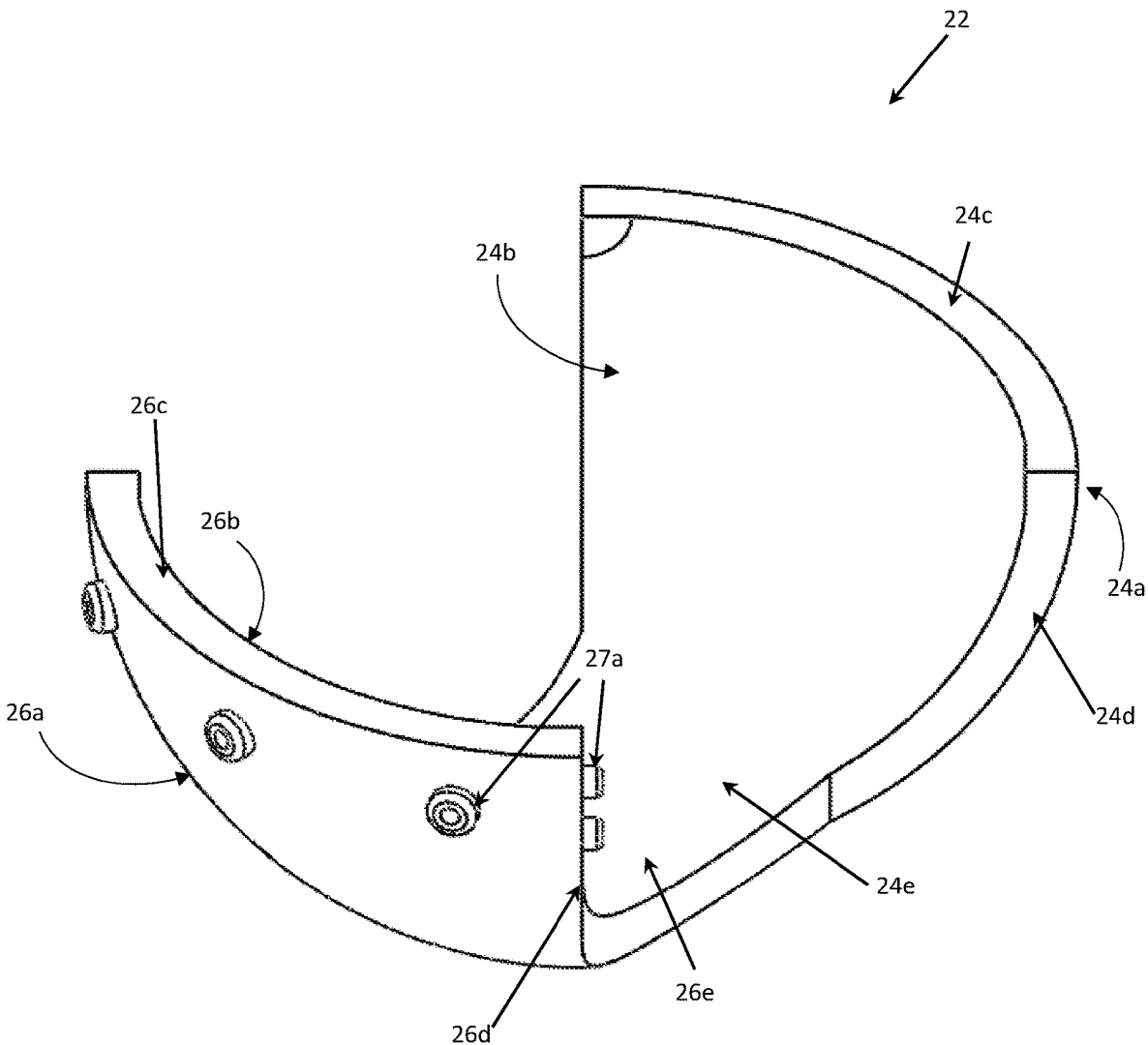
FIG. 6 is a perspective view of the diaper support of FIG. 4.

The diaper support 22 can have a single panel 22a having a back portion 24 configured to cover the bottom area of the wearer when the garment 20 is worn, and a front portion 26 configured to cover a pelvic area of the wearer when the garment 20 is worn. The back and the front portions 24, 26 of the single panel 22a have an outer face 24a, 26a and an inner face 24b, 26b (see FIG. 6). The portions 24, 26 of the panel 22a also have a top edge 24c, 26c, two side edges 24d, 26d and a lower part 24e, 26e. The back portion 24 of the panel 22a is connected to the inner side of the back part of the body 25 in proximity to the waist portion 23 along at least the top edge 24c. For example, the back portion 24 can be sewn or bonded to a back part of a garment body 25 along the top edge 24c. In one embodiment, the back portion 24 can also be connected to the body 25 along at least a portion of the two side edges of the body 25. For example, an upper portion of the two side edges 24d can be sewn along a portion of the side seams of the body 25. The lower part 24e of the back panel 24 and the lower part 26e of the front panel 26 are interconnected forming an integral single panel 22a. In one embodiment the back portion 24 and the front portion 26 can be two separated panels that are sewn or bonded together forming the single panel 22a.

The diaper support 22 further comprises a fastener 27 that can be a two-part fastener having a pair of fastening elements. A first element 27a can be positioned on the outer face 26a of the front portion 26 in proximity to the top edge 26c while a second element 27b of the fastener 27 is positioned at the inner side of the front part of the body 25 of the garment 20 along a part of the waist portion 23 and along the two side seams of the body 25 and at a position to correspond to the position of the first element 27a. In one embodiment, the first element 27a of the fastener 27 can be positioned in proximity to a portion of the two side edges 26d of the front panel 26 and the second element of the fastener 27 can be positioned in proximity to a corresponding matching position at a portion of the two side seams of the body facing the two side seams 26d. Persons skilled in the art understand that the second element 27b of the fastener can be positioned at the inner side of the body while the first element 27a can be on the outer face of the front portion 26, or vice-versa, without departing from the scope of the invention.

The fastener 27 can be any suitable fastener, such as a snap fastener where the first element 27a can comprise a number of male parts of snap fastener while the second element 27b can comprise a number of matching female parts of the snap fastener or vice versa, or the fastener 27 can comprise a number of buttons and the corresponding openings/slits or a number of hook-and-eye pairs. For example, the two-part fastener 27 can be a snap fastener, a swan hook fastener, a Velcro® type of fastener, hook and loop fastener, hook and eye fastener, button and loop fastener, clasp and hook, or a buckle. In one embodiment, the two-part fastener 27 can be adjustable by having two or more numbers and/or rows of the first elements 27a and/or two or more numbers and/or rows of second elements 27b, so that a size of the diaper support 22 can be adjusted.

While particular elements, embodiments and applications of the present disclosure have been shown and described, it will be understood, that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The example calculations, simulations, results, graphs, values, and parameters of the embodiments described herein are intended to illustrate and not to limit the disclosed embodiments. Other embodiments can be configured and/or operated differently than the illustrative examples described herein.

The invention claimed is:

1. A garment for a baby, the garment comprising:
a body having a front part and a back part joint together forming a torso portion of the garment with a head opening and two arm openings, a lower portion having a closable opening along a bottom edge of the lower portion and a fastener to open and close the closable opening, and a waist portion between the torso portion and the lower portion of the garment, the body of the garment having an outer side and an inner side; and
an integrated diaper support having:
a back panel having an outer face and an inner face and comprising a top edge, two side edges and a lower part, the back panel connected to the inner side of the back part of the body of the garment at the waist portion along at least the top edge;
a front panel having an outer face and an inner face and comprising a top edge, two side edges and a lower part, the front panel connectable to an inner side of the front part of the body of the garment in proximity to the waist portion; and
a diaper support fastener spaced apart from the fastener of the closable opening of the lower portion of the body of the garment and having a first element secured to the outer face of the back panel and a second element secured to the inner face of the front panel of the diaper support in proximity to a lower part edge of the inner face of the front panel, wherein when the first and the second elements of the diaper support fastener are separated the diaper support is configured to be in an open configuration to allow a user to put on a diaper to be worn by a wearer and when the first and the second elements are engaged together the diaper support is configured to be in a closed configuration for supporting a weight of the diaper worn by the wearer, a lower part of the diaper support being spaced apart from the lower portion of the body of the garment when the diaper support is in the closed configuration.

2. The baby garment of claim 1, wherein the outer side of the front panel is connected to the inner side of the front part of the body in proximity to the waist portion of the body.

3. The body garment of claim 1, wherein the first element of the support fastener comprises a number of male parts while the second element comprises a number of matching female parts.

4. The body garment of claim 3, wherein the diaper support fastener is adjustable by having two or more rows of male parts and/or two or more rows of female parts.

5. The body garment of claim 1, wherein the diaper support fastener is a snap fastener, a swan hook fastener, a hook and loop fastener, a hook and eye fastener, a button and loop fastener, a clasp and hook fastener, or a buckle.

6. The baby garment of claim 1, wherein the back panel is connected to the inner side of the back part of the body along at least a portion of the two side edges of the back panel.

7. The baby garment of claim 6, wherein the front panel is connected to the inner side of the front part of the body along at least a portion of the two side edges of the front panel.

8. A diaper support comprising:

a back panel having an outer face and an inner face and comprising a top edge, two side edges and a lower part, the back panel connected to the inner side of a back part of a garment along a waist portion;

a front panel having an outer face and an inner face and comprising a top edge, two side edges and a lower part, the front panel connectable to an inner side of a front part of the garment along the front part of the waist portion; and a diaper support fastener having a first element secured to the outer face of the back panel of the diaper support in proximity to a lower part edge of the outer face of the back panel and a second element secured to the inner face of the front panel of the diaper support in proximity to a lower part edge of the inner face of the front panel, when the first and the second elements are separated the diaper support is configured to be in an open configuration to allow a user to put on a diaper and when the first and second elements are joined together the diaper support is configured to be in a closed configuration for supporting a weight of the diaper.

9. The diaper support of claim 8, wherein the first element of the fastener comprises a number of male parts of a snap fastener while the second element comprises a number of matching female parts of the snap fastener.

\* \* \* \* \*